United States Patent [19]

Alter et al.

[11] Patent Number: 5,753,094
[45] Date of Patent: May 19, 1998

[54] BORATE STORAGE BUFFER AND SAMPLE DILUENT

[75] Inventors: Stephen C. Alter, Tustin; Elsie H. Kim, Irvine, both of Calif.

[73] Assignee: Beckman Instruments, Inc., Fullerton, Calif.

[21] Appl. No.: 530,957

[22] Filed: Sep. 20, 1995

[51] Int. Cl.$^6$ .................. G01N 27/26; G01N 27/447
[52] U.S. Cl. .................................... 204/451; 204/601
[58] Field of Search ............................ 204/451, 452, 204/453, 454, 455, 601, 602, 603, 604, 605

[56] References Cited

U.S. PATENT DOCUMENTS

| | | | |
|---|---|---|---|
| 3,062,731 | 11/1962 | Durrum | 204/469 |
| 3,497,437 | 2/1970 | Louderback et al. | 204/469 |
| 3,912,610 | 10/1975 | Lou | 436/516 |
| 4,159,895 | 7/1979 | Shine | 435/29 |
| 4,209,372 | 6/1980 | Bluestein et al. | 204/468 |
| 4,312,727 | 1/1982 | Shainoff | 204/469 |
| 4,558,007 | 12/1985 | Anderson et al. | 435/26 |
| 4,654,301 | 3/1987 | Anderson et al. | 435/26 |
| 4,857,163 | 8/1989 | Gurske et al. | 204/468 |
| 4,997,537 | 3/1991 | Karger et al. | 204/453 |
| 5,098,539 | 3/1992 | Shieh | 204/453 |
| 5,120,413 | 6/1992 | Chen et al. | 204/451 |
| 5,139,630 | 8/1992 | Chen | 204/451 |
| 5,228,960 | 7/1993 | Liu et al. | 204/451 |
| 5,310,462 | 5/1994 | Chen | 204/452 |
| 5,431,793 | 7/1995 | Wang et al. | 204/452 |

FOREIGN PATENT DOCUMENTS

| | | |
|---|---|---|
| 0135278 A2 | 3/1985 | European Pat. Off. . |
| 0494544 A2 | 7/1992 | European Pat. Off. . |

OTHER PUBLICATIONS

Ahmed, et al. "Antifreeze Glycoproteins from Antarctic Fish," Journal of Biological Chemistry, vol. 251, No. 10, May 25, 1976, pp. 3033-3036.

Baillet, et al. "Fosfomycin determination in serum by capillary zone electrophoresis with indirect ultraviolet detection," Journal of Chromatography, 616 (1993), pp. 311-316, Biomedical Applications, Elsevier Science Publishers B.V., Amsterdam. No month available.

Thormann, et al. "Determination of substituted purines in body fluids by micellar electrokinetic capillary chromatography with direct sample injection," Journal of Chromatography, 593 (1992), pp. 275-288, Elsevier Science Publishers B.V., Amsterdam. No month available.

Chen, Fu-Tai A., "Rapid protein analysis by capillary electrophoresis," Journal of Chromatography, 559 (1991), pp. 445-453, Elsevier Science Publishers B.V., Amsterdam. No month available.

Cann, John R., "Multiple Electrophoretic Zones Arising from Protein-Buffer Interaction," Biochemistry, vol. 5, No. 3, Mar. 1966, pp. 1108-1112.

Kawasaki, et al., "Quantitative Immunoassay of Human Deoxycytidine Kinase in Malignant Cells," Analytical Biochemistry 207, pp. 193-196 (1992). No month available.

Pande, et al., "Optimization and Validation of Analytical Conditions for Bovine Serum Albumin Using Capillary Electrophoresis," Analytical Biochemistry 204, pp.103-106 (1992). No month available.

Winter, et al., "4-Methyleneglutamine Amidohydrolase from Peanut Leaves," Plant Physiol. No month available (1991) 95, pp. 206-212.

Chen, et al., "Characterization of proteins by capillary electrophoresis in fused-silica columns: Review on serum protein analysis and application to immunoassays," Electrophoresis 1994 No month available, 15, pp.13-21.

"High-Performance Capillary Electrophoresis Of Glycoproteins: The Use Of Modifers Of Electroosmotic Flow For Analysis Of Microheterogeneity," James P. Landers et al., Analytical Biochemistry 205, 115-124 (1992). No month available.

"Capillary Electrophoresis—a New Clinical Tool," Fu-Tai A. Chen et al., Clinical Chemistry, vol. 37, No. 1, 1991. No month available.

"Effect of buffer constituents on the determination of therapeutic proteins by capillary electrophoresis," Guzman et al., Journal of Chromatography, 608 No month available (1992) 197-204.

"Influence of Borate Complexation on the Electrophoretic Behavior of Carbohydrates in Capillary Electrophoresis," Sabrina Hoffstetter-Kuhn et al., Anal. Chem. No month available 1991, 63, 1541-1547.

Sumiko Suzuki et al, "Determination of synthetic food dyes by capillary electrophoresis" Journal of Chromatography A, 680 No month available (1994) 541-547.

(List continued on next page.)

*Primary Examiner*—Kathryn L. Gorgos
*Assistant Examiner*—John S. Starsiak, Jr.
*Attorney, Agent, or Firm*—William H. May; Margaret A. Kivinski

[57] ABSTRACT

A composition, which has utility as a storage buffer and as a sample diluent before analysis by capillary zone electrophoresis (CZE), is comprised of water, a borate compound, a buffer compound and a pH modifier for maintaining a physiological pH. In addition, a conductivity adjusting compound is present so that the conductivity of the composition is about the same as a prospective capillary electrophoresis running buffer. Containers with storage buffer/sample diluent can be assembled in a kit for conducting serum protein electrophoresis (SPE) or immunosubtraction (IFE/s) analysis. Moreover, the storage buffer/sample diluent can be used in methods of preparing samples for CZE analysis, such as quantitative dilutions and enzymatic or immunological reactions.

47 Claims, 4 Drawing Sheets

OTHER PUBLICATIONS

Wolfgang Thurmann et al, "Determination of thiopental in human serum and plasma by high-performance capillary electrophoresis-micellar electro-kinetic chromatography" Journal of Chromatography, 559 No month available (1991) 505–513.

S.F.Y. Li et al, "Retention of eleven priority phenols using micellar electrokinetic chromatography" Journal of Chromatography, 516 No month available (1990) 263–270.

Hiroto Ozaki et al, "Micellar electrokinetic chromatography using high-molecular surfactants Use of butyl acrylate-butyl methacrylate-methacrylic acid copolymers sodium salts as pseudo-stationary phases" Journal of Chromatography A 680 (No month available 1994) 117–123.

S.F.Y. Li et al, "Separation of Dns-amino acids and vitamins by micellar electrokinetic chromatography" Journal of Chromotography, 559 (No month available 1991) 537–545.

Liisa Mälkki-Laine et al, "Electrokinetic behaviour of salbutamol and its decomposition products and determination of salbutamol by micellar electrokinetic capillary chromatography" Journal of Chromatography A 726 No month available (1996) 297–306.

J.D. McCulloch, "Egg White Protein Separation Development: Effect of Buffers and Untreated Fused Silica Vs. Neutral Covalently Bonded Columns" Journal of Liquid Chromatography, 16(9 & 10), No month available (1993) 2025–2038.

Mark Greenaway et al, "Micellar electrokinetic chromatographic studies in $D_2O$ based buffer solutions" Electrophoresis, 15 No month available (1994) 1284–1289.

Ching-Erh Lin et al, "Migration behavior and selectivity of dichlorophenols in micellar electrokinetic capillary chromatography Influence of micelle concentration and buffer pH" Journal of Chromatography A, 722 (No month available 1996) 333–343.

BORATE STORAGE BUFFER AND SAMPLE DILUENT

BACKGROUND

Protein analysis of clinical samples, such as whole blood, serum, plasma, cerebrospinal fluid, and urine, can provide valuable information to the investigator. For example, elevated or depressed levels of certain protein components of serum, such as albumin, alpha-1 lipoprotein, alpha-2 macroglobulin, beta-1 lipoprotein, and immunoglobulins (including gamma globulins) can indicate an underlying disease state or bodily condition.

A typical example is albumin, the major protein of serum. Albumin is usually present in a concentration of between 3.2 and 5.0 g/dl. Decreased concentrations of albumin can be indicative of renal disease, whereas increased concentrations of albumin are characteristic of dehydration. A second example is elevated alpha-1 lipoprotein, which can be indicative of chronic alcoholism or hyperestrogenism due to, e.g. pregnancy. An additional example is elevated levels of beta-1 lipoprotein, which can be indicative of increased cholesterol.

Analysis of the amount and type immunoglobulins is particularly important in the diagnosis of "monoclonal gammopathies". These abnormalities are characterized by immunoglobulins of the same idiotype, which are produced at elevated levels by single, unregulated B-cell clones. Monoclonal gammopathies do not necessarily cause clinical disorders in an individual. Such a situation can be referred to as "benign monoclonal gammopathy" or "monoclonal gammopathy of undetermined significance". However, many clinical disorders are associated with monoclonal gammopathy. For example, monoclonal IgM, i.e. an increase in the production of an IgM idiotype by unregulated B-cell clones, is associated with the disease Waldenstrom's macroglobulinemia. Because IgM has a relatively high molecular weight, increased production of IgM is associated with an increased viscosity of the patient's blood, referred to as "hyperviscosity". Hyperviscosity is associated with symptoms, such as headache, dizziness and vertigo.

Multiple myeloma is another clinical disorder associated with monoclonal gammopathy, which can manifest as an increase in IgG, IgA, IgD, or IgE idiotypes. Moreover, kappa or lambda light chains, or gamma, alpha, mu, or delta heavy chains may be elevated. A major pathologic feature of multiple myeloma is bone destruction, i.e. bone deformity or acute, painful pathological fractures. Clinically, the patient may experience bone pain, infections due to decreased production of normal Ig's, and anemia. Twenty percent of myeloma patients produce Bence Jones proteins, which are free monoclonal light chains. Because of their relatively small size Bence Jones proteins are typically excreted in patient urine. Multiple myeloma can also impact neural tissue, i.e. the spinal cord, nerve roots and cranial or peripheral nerves.

Serum proteins, including immunoglobulins, can be separated from each other using electrophoretic methods, typically gels subjected to an electric field. In a similar manner, proteins from clinical samples can also be analyzed using capillary zone electrophoresis ("CZE"). See, for example, Chen, Fu-Tai A., et al. "Capillary Electrophoresis—A New Clinical Tool." *Clin. Chem.* 77/1:14–19 (1991); see also, U.S. Pat. No. 5,120,413. Both these documents are incorporated herein by reference.

The CZE technique permits rapid and efficient separations of charged substances, including proteins. Separation of the constituents of clinical samples can be accomplished in less than 20 minutes, typically in less than 10 minutes. In general, CZE involves introduction of a liquid sample into a capillary tube filled with an electrolytic running buffer. The capillary tube typically has an internal diameter of from about 2 to about 2000 microns ("μm"). Application of an electric field to the tube both pulls the sample through the tube and separates it into its constituent parts. As a result, the constituents of the sample are resolved into discrete zones in the capillary tube during their migration through the tube. An on-line detector can be used to continuously monitor the separation and provide data as to the various constituents based upon the discrete zones.

The composition of running buffer is an important factor in CZE separations. Borate compounds, in particular, have proved useful as constituents of CZE running buffers. In addition to providing low conductivity and sufficient buffering capacity over the pH range of about 8 to 11, borates can form stable complexes with sugar residues on glycoproteins. Consequently, the electrophoretic mobility of a glycoprotein is modified, eluting as a later peak than an unmodified protein counterpart. Since complexation of sugar moieties is strongly dependent on the buffer pH and the borate concentration, both parameters can be adjusted for optimization of an electrophoresis buffer. In general, a higher pH and higher borate concentration results in a higher proportion of the complexed species and in a more negative net charge. Examples of borate containing electrophoresis buffers can be found in U.S. Pat. No. 5,120,413, which is incorporated herein by reference.

The specificity of binding associated with antibodies and their receptive antigenic binding partner(s) has also been used extensively to identify clinically significant proteins. Immunoelectrophoresis, Immunofixation Electrophoresis, and Immunosubtraction Electrophoresis (IFE/s) are examples of immunological methods that are used in conjunction with an electrophoretic separation step. In particular, IFE/s has been adapted to exploit the both the speed of capillary electrophoresis and the specificity of immunological reactions involving antigens and antibodies. See for example, U.S. Pat. No. 5,228,960, which is incorporated herein by reference.

During IFE/s, a clinical sample is pre-incubated with a specific binding partner directed to a sample constituent. The specific binding partner is typically an insolubilized immunoglobulin, which can be substantially removed from the sample. A comparison of sample aliquots, which have or have not been subjected to immunosubtraction, are compared by CZE analysis. Binding of the insolubilized specific binding partner can result in a reduction in the level of an elevated sample constituent. Thus, immunosubtraction can establish the sample constituent's identity. This method is particularly useful in the identification and typing of monoclonal gammopathies.

Clinical samples are generally diluted prior to analysis by capillary electrophoresis. Such dilution facilitates inter alia, achieving a desired analytical ratio, and further aids in utilization of the sensitivity associated with capillary electrophoresis analysis. An undiluted clinical sample, particularly serum, can provide too much protein component, making analysis difficult. When clinical specimens are analyzed directly by capillary electrophoresis, the diluent is typically chosen to be compatible with the pH and conductivity of the electrophoresis buffer. Alternatively, when biochemical processes, such as enzymatic or immunological reactions, are conducted prior to electrophoretic analysis, a lightly buffered saline diluent, which does not effect the reaction components in a deleterious manner, is generally appropriate.

Preliminary screenings for serum protein abnormalities are frequently done by serum protein electrophoresis (SPE). In the event that a suspected abnormality is detected, a second immunological or enzymatic test can be performed for a more definitive diagnosis. For example, immunosubtraction (IFE/s) may be used to follow-up an SPE analysis when a monoclonal gammopathy is suspected. Moreover, the IFE/s or enzymatic procedure typically includes a concurrent SPE-type separation for comparison purposes.

Since SPE and IFE/s electropherograms are subject to direct comparison, it would be beneficial if the buffers and diluents used to prepare samples for CZE analysis were substantially identical. The ideal storage buffer would be compatible with the IFE/s requirements for storing immunological reagents and performing immunosubtraction reactions. Moreover, the ideal sample diluent would be compatible with the running buffer used for the CZE analysis step of SPE and IFE/s. The use of a substantially identical storage buffer/sample diluent for SPE and IFE/s would help to eliminate any inconsistent results that are observed for the two methods. In addition,the use of a single sample diluent/ storage buffer for both methods introduces a cost-effective simplification of storage, manufacturing, packaging, and documentation procedures.

SUMMARY

The present invention meets the need for a composition that can be used both as a storage buffer and for sample diluent prior to capillary electrophoresis, thereby eliminating the need for separate formulations. The composition is comprised of: (a) water; (b) a borate compound present in an amount of about 5 to 150 mM; (c) a buffer compound and a pH modifier present in an amount sufficient to adjust the pH to between about 6 to 8; and (d) a conductivity adjusting compound present in an amount sufficient to adjust the conductivity of the composition to between about 5 to 8 mMho.

The borate compound can be sodium tetraborate or boric acid. Buffer compound is typically present in an amount of about 5 to 25 mM. Preferred buffer compounds can be chosen from the group consisting of sodium phosphate, potassium phosphate, sodium acetate, and 2-[tris (hydroxymethyl)methyl]amino-ethanesulfonic acid (TES). The pH modifier is usually sodium hydroxide, hydrochloric acid, or potassium phosphate.The conductivity adjusting compound is typically present in an amount of about 1 to 150 mM and can be selected from the group consisting of sodium chloride, potassium chloride, and a mixture of sodium chloride and potassium chloride.

The clinical samples prepared for electrophoretic analysis can be whole blood, plasma, serum, urine, or cerebrospinal fluid. Sample constituents of particular interest include human immunoglobulins, transferrin, beta-lipoprotein, and C3-complement.

The storage buffer/sample diluent can also contain at least one external marker which can be either an ionic or neutral charge species, to aid in the identification and/or quantitation of constituent peaks during electrophoretic analysis. Ionic species can be selected from the group consisting of formic acid, acetic acid, benzo-phosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, trichlorobenzoic acid, naphthyl sulfonic acid, benzo naphthalinic acid, chloro-benzo naphthalinic acid, chloro-naphthyl sulfonic acid, tetra-iodo benzo naphthyl sulfonic acid, and di-iodo anthracenyl sulfonic acid. Neutral charge species can be benzyl alcohol, mesityl oxide, isopropanol, methanol, ethanol, ethylene glycol, dimethylformamide (DMF), formamide, protected peptides or protected amino acids.

When the composition is used in preparation for capillary electrophoresis immunosubtraction, it further comprises at least one specific binding partner to a sample constituent. Preferably, the specific binding partner is capable of being substantially removed from the composition, e.g. by binding to an insolubilized material. Anti-human antibody is particularly useful specific binding partner for diagnostic purposes, especially anti-human immunoglobulin antibody.

A preferred embodiment of the storage buffer/sample diluent comprises a) water; b) sodium tetraborate present in an amount of about 10 mM; c) sodium phosphate present in an amount of about 20 mM; d) sodium chloride present in an amount sufficient to adjust the conductivity of the composition to about 7 mMho; and e) a pH modifier present in an amount sufficient to adjust the pH to about 7.

The composition can be a component in test kits used for sample preparation prior to serum protein electrophoresis (SPE) or capillary electrophoretic immunosubtraction (IFE/ s). The SPE kits can include a first container, which contains the borate containing sample diluent described above, and a second container for retaining the sample(s) during dilution. The IFE/s kit can include a first container, which includes sample diluent without any specific binding partner, and a second container having storage buffer/sample diluent that does include a specific binding partner.

Moreover, the composition can be used in methods of preparing samples prior to SPE and IFE/s. The methods can include the steps of measuring an aliquot of a clinical sample and diluting the sample with 1 to 300 parts of the storage buffer/sample diluent.

DRAWINGS

These and other features, aspects, and advantages of the present invention will become better understood with regard to the following description, appended claims, and accompanying drawings where:

DESCRIPTION

The present invention is a composition with utility as both a storage buffer and a diluent for samples and biochemical reagents before CZE analysis. The composition includes water, a borate compound, a buffer compound and a pH modifier for maintaining a physiological pH. In addition, a conductivity adjusting compound is present so that the conductivity of the solution is about the same as a prospective capillary electrophoresis running buffer. Containers with storage buffer/sample diluent can be assembled in a kit for conducting serum protein electrophoresis (SPE) or immunosubtraction (IFE/s) analysis. Moreover, the storage buffer/sample diluent can be used in methods of preparing samples for CZE analysis, such as quantitative dilutions and enzymatic or immunological reactions.

A. Borate Compound

The addition of a borate compound to clinical samples prior to capillary electrophoresis results in a surprising improvement in the resolution and reproducibility of subsequent electrophoretic analyses. Applicants believe that because many of the proteins found in clinical samples are glycoproteins, the complexation of borate with sugar moieties may play a role in this unexpected improvement. This is particularly advantageous, because a borate containing composition can be used as a storage buffer for biochemical reagents and as a diluent for clinical samples. The subsequent improvement in the electrophoretic resolution permits a reliable comparison between clinical samples before and after a biochemical reaction directed to a component of the sample.

The borate compound is typically boric acid or sodium tetraborate, which is present in the composition at a minimum concentration of 20 mM or 5 mM, respectively. No improvement in electrophoretic resolution is observed at lower concentrations of borate. Similarly, no additional improvement in electrophoretic resolution is observed at boric acid or sodium tetraborate levels greater than about 160 mM or 40 mM, respectively. Preferably boric acid is present in an amount between about 30 to 80 mM or sodium tetraborate is present in an amount of between about 10 to 20 mM. A most preferred concentration of boric acid is about 40 mM and a most preferred concentration of sodium tetraborate is 10 mM. These concentrations give the most reproducible serum protein patterns during capillary electrophoresis, particularly in the Beta region.

B. Buffer Compound

Consistent with the composition's use as a storage buffer for biochemical reagents, the pH of the solution contains a buffer compound, with an effective buffering range of about 6 to 8. This pH range does not inactivate the biological activities of specific binding partners, such as antibodies and antigens or enzymes and substrates. Moreover, assay reagents frequently utilize organic linkages between a biomolecule and solid phase material, e.g. an antibody linked to agarose through a CNBr-activated linkage. These linkages are less susceptible to hydrolysis at about pH 7 than at higher pH.

Suitable buffer compounds include sodium phosphate, potassium phosphate, sodium acetate, and 2-[tris(hydroxymethyl)methyl]amino-ethanesulfonic acid (TES). A preferred buffer compound is TES, which has a suitable buffering capacity within the desired pH range. However, the most preferred buffer compound is sodium phosphate, which is compatible with standard phosphate buffered saline formulations. The buffer compound is typically present in an amount of about 5 mM to 25 mM. The most preferred concentration of TES is about 10 mM and the most preferred concentration of sodium phosphate is about 20 mM. A sufficient amount of a pH modifier, such as sodium hydroxide, hydrochloric acid, or potassium phosphate, is added to the composition to bring the pH within about 6 to 8, preferably within 6.5 to 7.5, and most preferably about pH 7.

C. Conductivity Adjusting Compound

For the best resolution of sample constituents, the conductivity of the composition should be roughly equivalent to that of the prospective capillary electrophoresis running buffer. This helps to alleviate potential problems with peak asymmetries or broadening. These peak anomalies can develop when a conductivity gradient exists at the boundary between the sample and the separation compartments of the capillary.

A typical electrophoresis running buffer is 150 mM borate, pH 10, which has a conductivity of about 7 mMho. The conductivity of the present invention is adjusted to be between about 5 to 8 mMho, most preferably about 7 mMho. This may be accomplished by adding sodium chloride, potassium chloride, or a mixture of sodium chloride and potassium chloride in an amount up to about 150 mM. A preferred concentration range for the conductivity adjusting compound is between about 30 to 120 mM and a most preferred concentration is about 75 mM.

D. Clinical Samples and Sample Constituents

The clinical samples that are prepared for analysis by SPE or IFE/s can be whole blood, plasma, serum, urine, or cerebrospinal fluid. Sample constituents to be separated typically include serum proteins, such as albumin, $\alpha_1$ globulin, $\alpha_2$ globulin, complement, beta-lipoprotein, and transferrin. Immunoglobulins are sample constituents of particular interest for the diagnosis of monoclonal gammopathies. The immunoglobulins include gamma, mu, alpha, delta and epsilon classes of heavy chains as well as kappa and lambda light chains. As described in more detail below, sample constituents can provide specific binding sites for specific binding partners, e.g. antigens for anti-human immunoglobulin antibodies, during IFE/s.

E. External Markers

For convenience, the sample diluent can include external markers, which are separable from sample constituents during CZE analysis. The external markers can include an ionic species and/or a neutral charge species that assist in the identification and/or quantitation of sample constituents. A neutral charge species has a net charge of zero and will have a faster relative mobility than negatively charged species during CZE. Thus, the neutral charge species will appear before all other electropherogram peaks during CZE. By "ionic species" is meant a negatively charged species having a charge density greater than that of each of the major constituents of the sample. Consequently the ionic species is detected after all of the major constituent peaks during CZE. Methods for using external markers to identify and quantify sample constituents are described in U.S. Pat. Nos. 5,139,630 and 5,228,960, respectively, which are incorporated herein by reference. The ionic species can be selected from the group consisting of formic acid, acetic acid, benzophosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chloro-benzo naphthalinic acid, chloro-naphthyl sulfonic acid, tetra-iodo benzo naphthyl sulfonic acid, and di-iodo anthracenyl sulfonic acid. In addition, the neutral charge species can be selected from the group consisting of mesityl oxide, isopropanol, methanol, ethanol, ethylene glycol, dimethylformamide (DMF), formamide, protected peptides and protected amino acids. A most preferred ionic species is 2,4,6 trichlorobenzoic acid and a most preferred neutral species is benzyl alcohol. The markers are preferably present in the sample diluent at about 0.6 g/liter for 2, 4, 6 trichlorobenzoic acid and about 2.0 ml/liter for Benzyl alchhol.

F. Specific Binding Partners

A specific binding partner to a sample constituent of interest can be beneficially included in the storage buffer. Examples of specific binding partners include antibody which binds to an antigen or an enzyme which binds to a substrate. The specific binding partner can be soluble or insoluble. Focusing on the antibody example, the specific binding partner is preferably insoluble and will have a tendency to settle at the bottom of a reaction vessel. Insoluble specific binding partners can be formed by coupling the specific binding partner to a solid support. The selection of a solid support is discretionary with the investigator, however a preferred solid support is cyanogen bromide activated Sepharose ™ (Pharmacia). Anti-human immunoglobulin (heavy or light chain) antibodies are available from commercial sources, e.g. DAKO Co. These antibodies can be coupled directly to the aforementioned solid support. With respect to IgG sample constituents, an alternative insoluble specific binding partner is agarose coupled Protein G (Pharmacia). As those in the art appreciate, Protein G is a cell surface protein isolated from group G Streptococcus which specifically binds to IgG from a number of mammals, including humans. However, anti-human IgG antibodies can be utilized with substantially equivalent efficiency.

G. SPE Kit

A serum protein electrophoresis (SPE) kit can be prepared that includes one or more containers filled with a preferred version of the sample diluent. For example, a first container can be filled with sample diluent lacking external markers and a second container can be filled with sample diluent having external markers. In addition, the kit can contain at least one sample receptacle that can be used to perform dilutions. The sample receptacle can have multiple chambers for performing multiple dilutions of the same or different samples.

H. IFE/s Kit

Similarly, an immunosubtraction (IFE/s) kit can be prepared that includes one or more containers filled with the sample diluent. Moreover, another container can include at least one specific binding partner in the storage buffer. A preferred IFE/s kit has a first container filled with sample diluent and a second container, which has multiple chambers containing different specific binding partners. For example, a most preferred IFE/s kit has a second container with anti-κ, anti-λ, anti-IgG, anti-IgA, and anti-IgM immunoglobulins in separate chambers.

I. How to Make

A standard recipe can be used to prepare sample diluents by combining various stock solutions. The stock solutions can include: 100 mM NaCl; 100 mM NaCl plus 2-fold concentrated markers, i.e., 0.2 g/L 2,4,6-trichlorobenzoic acid (TCBA) and 0.8 g/L Benzyl alcohol; and 100 mM solutions of each buffer compound adjusted to the desired pH. Diluents with 10 mM buffer compound plus 70 mM NaCl can be prepared by combining 1 part of concentrated buffer compound, 5 parts of 100 mM NaCl plus markers, 2 parts of 100 mM NaCl alone, and 2 parts deionized $H_2O$. Conductivity measurements can be made with, e.g. a YSI Model 35 Conductivity Meter. This standard recipe produces diluents with a conductivity of approximately 5.6 mMho. By comparison, the conductivity of running buffer is about 7.0 mMho.

In order to prepare diluents at a conductivity equal to that of the Running Buffer, solutions containing sodium phosphate, potassium phosphate, sodium acetate, or "Good Buffers" such as TES and varying concentrations of sodium tetraborate or boric acid can be supplemented with differing amounts of additional NaCl. For example, 10 mM NaCl gives a measured conductivity of about 0.9 mMho. These diluents can be prepared by dissolving measured amounts of buffer salt and sodium tetraborate or boric acid in 90 mL deionized water, adjusting to the desired pH with 1.0 M NaOH or HCl, and adjusting the volume to 100 mL. The conductivity of the solution is then measured and applied to the equation:

$$[7 \text{ mMho} - (\text{conductivity of solution})]/9 = X$$

where X is the amount of NaCl, in millimoles, needed to raise the conductivity to equal Running Buffer. The required amount of crystalline NaCl is added and the conductivity is measured again. 7.0 mMho±0.7 is considered acceptable. No sodium chloride is added when the concentration of borate, and consequently the conductivity, is greater than 150 mM borate Running Buffer.

J. How to Use

The composition can be used as sample diluent for SPE. An aliquot of a clinical sample is mixed with 1 to 100 parts of the storage buffer/sample diluent, depending on the sample. For example the protein concentration for a serum sample of a healthy individual is about 60 mg/ml. Similar concentration values for urine and cerebrospinal fluid (CSF) are about 10 µg/ml and between about 150 and 400 µg/ml, respectively. Focusing on serum, dilution is typically from 1 part sample to about 9 parts diluent (1:10=0.1) up to about 1:100 (0.01). A 1:20 serum dilution is most preferred. Urine and CSF samples may require a concentration procedure and/or dialysis against the sample diluent to give protein concentrations roughly equivalent to those of serum samples.

The composition can also be used as a sample diluent and/or storage buffer in an IFE/s procedure, as in U.S. Pat. No. 5,228,960, which is incorporated herein by reference. Typically, a serum sample is pre-diluted at, e.g. 1:2, 1:7 or 1:15. One part of the pre-diluted serum is then combined with 5 to 100 parts of a solid stage suspension, which is generally referred to as a "gel slurry". The solid suspension is typically comprised of an insoluble specific binding partner, e.g. antibody attached to agarose, suspended in storage buffer/sample diluent. Dilutions can be adjusted to give a desired ratio of sample constituent to specific binding partner in the mixture. The mixture is incubated and the insolubilized specific binding partner is allowed to settle to the bottom of the reaction vessel. The "immunosubtracted" supernatant is then subjected to CZE analysis.

K. Advantages of the Invention

The previously described versions of the present invention have many advantages. For the composition, these include the convenience of having a single formulation that can be used for storing reagents, conducting biochemical reactions, and diluting samples prior to CZE analysis. In addition, the inclusion of borate compounds in the formulation has the surprising effect of improving the resolution of serum proteins by CZE analysis. The reproducibility of the improved separation allows a reliable comparison of electropherograms from related CZE analyses, like SPE and IFE/s. Moreover, the use of a common buffer for these related procedures introduces economies of scale in the manufacture of reagents as well as convenient packaging alternatives, such as the SPE and IFE/s kits.

EXAMPLES

Prior to the adoption of the present invention, capillary electrophoresis separation steps during SPE and IFE/s displayed slight differences in the migration and resolution of some serum proteins, making comparisons between methods difficult. The cause of the differences was that samples were introduced in different environments. For SPE, the sample was diluted in pH 10.0 Borate buffer then injected. For IFE/s, the sample was pre-diluted in a borate buffer (pH 10.0 or 10.2) or a phosphate buffer (pH 7.0) and then further diluted in the Solid Phase Storage Buffer (phosphate buffered saline, pH 7.0). Even though the same running buffer was used, injecting the sample in buffers that differ in chemical makeup and pH produced different electropherograms. Additional considerations, such as optimal instrument design and reagent packaging, provided further impetus to find a common storage buffer/sample diluent.

Materials

Sodium chloride, sodium tetraborate (decahydrate), and monobasic sodium phosphate were products of Mallinckrodt Specialty Chemicals, Paris, KY. Sodium azide was a product of BDH Laboratory Supply, Poole, England. Benzyl alcohol was obtained from Sigma Chemical Company, and 2,4,6-trichlorobenzoic acid was obtained from Aldrich Chemical Company, both of St. Louis, Mo. TES (sodium salt), i.e., 2-{[tris-(hydroxymethyl)-methyl]-amino}-ethanesulfonic acid was obtained from Calbiochem, San Diego, Calif.

"ICS Diluent" is a product of Beckman Instruments, Brea, Calif., and consists of 20 mM potassium phosphate, 75 mM sodium chloride, and 0.1% (w/v) sodium azide, pH 7.0. It was used in this study as a "generic" phosphate buffered saline.

"ICS Buffer" is ICS Diluent supplemented with 4% polyethylene glycol (PEG).

"ID ZONE" is a serum control product of Beckman Instruments, and contains ethylene glycol as a preservative. This material was used as the serum sample for these studies.

Reagents for capillary electrophoresis included: Running Buffer comprised of 37.5 mM sodium tetraborate, pH 10.0, which is also referred to as 150 mM borate; a Cleaning Solution of 0.2 N NaOH, which was used to clean capillaries between runs; and Solid Phase Storage Buffer, which consists of 20 mM sodium phosphate, 75 mM sodium chloride, and 0.1% (w/v) sodium azide, pH 7.0.

In this study, various formulations were tested for the "Sample Diluent". The Sample Diluent can be the vehicle whereby two external markers are added to the sample. Benzyl alcohol (0.4 mL per liter) and 2,4,6 trichlorobenzoic acid (0.1 g per liter) were added to certain test Diluents as external markers.

Experimental Methods

Tests were performed on a prototype instrument, identified as "CALCITE" (Beckman Instruments, Inc., Fullerton, Calif.). This instrument has six parallel untreated fused silica capillaries, each measuring 25 μm×by 20.4 cm or 22.4 cm with a separation length of 18 or 20 cm respectively. The outer surfaces of the capillaries were coated with polyimide to protect the capillaries from breakage (Polymicro Technologies, Inc., Phoenix, Ariz.). An optics module, including a UV light source (deuterium lamp) and a 214 nanometer filter, as well as a detector, was aligned with an aperture, located at 2.4 cm from a capillary tube outlet. Each capillary ran the same samples and diluent so that cross-capillary variation could be observed and eliminated from the analysis.

To mimic standard SPE conditions, one part ID ZONE sample plus 9 parts diluent, i.e., a 1:10 dilution, was injected with one second of vacuum. Electrophoresis was performed at 9000 Volts for 5 minutes.

To simulate standard IFE/s conditions, one part ID ZONE sample was diluted with one part diluent. The pre-diluted sample (20 μl) was then further diluted with 160 μl of storage buffer. The fully diluted sample was injected with a one second vacuum and subjected to electrophoresis at 7,600 volts for 6 minutes.

The resulting electropherograms were evaluated unnormalized using the AUTO-CAP Version 2.04 software tool (Beckman Instruments, Inc., Fullerton, Calif.) and compared visually for reproducibility and resolution of the various peaks and shoulders.

Example 1
Buffer Compounds and pH

An experiment was conducted to see if the differences in peak morphology observed during SPE versus IFE/s separation steps was caused by different buffer compounds (borate vs. phosphate) or by differences in the pH. The following buffer solutions were prepared:

1) 150 mM borate, pH 7.0 (boric acid)

2) 150 mM borate, pH 10.0 (37.5 mM sodium tetraborate)

3) 20 mM potassium phosphate dibasic, pH 7.0 75 mM sodium chloride 4) 20 mM potassium phosphate dibasic, pH 10.0 75 mM sodium chloride In order to mimic the conditions for IFE/s electrophoresis, 10 μl of a serum sample was diluted with 170 μl of each of the above listed buffers. Electrophoresis was conducted at 7.6 kV for 6 minutes using 150 mM borate, pH 10.0 as Running Buffer.

Figure 1A:
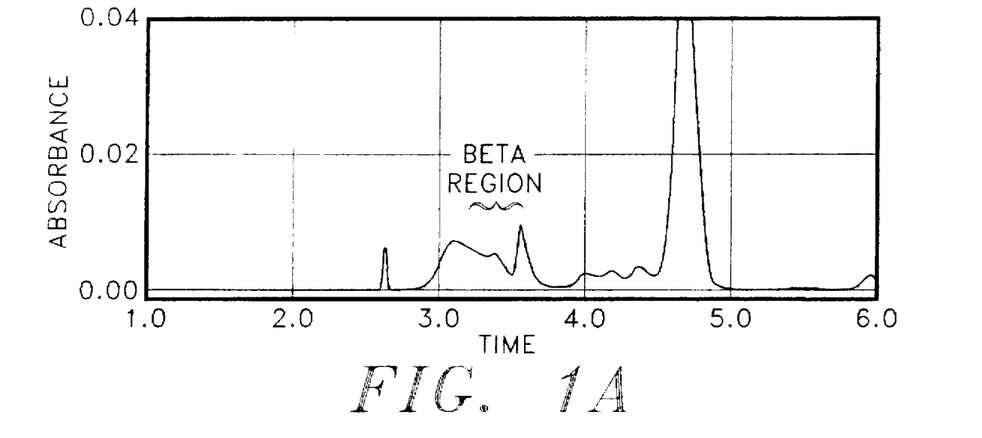
FIG. 1A is an electropherogram of a normal control serum sample diluted in 150 mM borate buffer, (37.5 mM sodium tetraborate), pH 10.0, with benzyl alcohol and trichlorobenzoic acid markers, separated into its constituents by CZE.
Figure 1B:
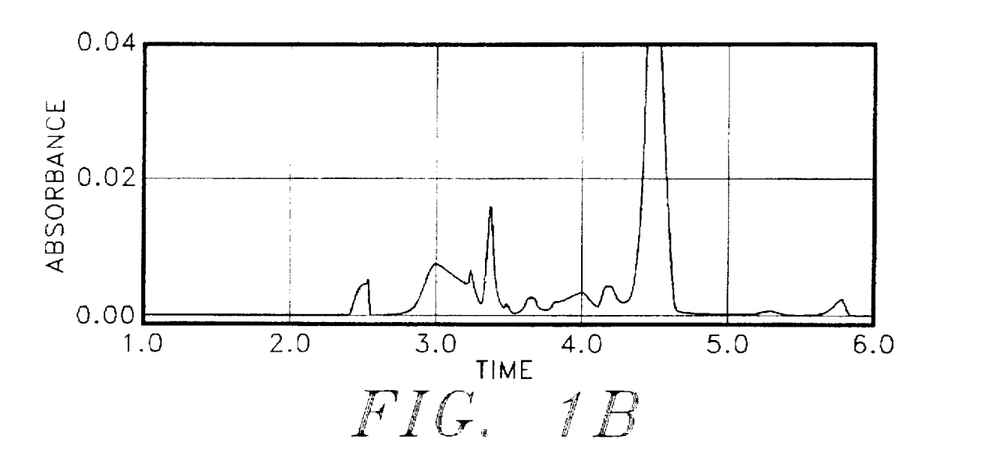
FIG. 1B is an electropherogram of a normal control serum sample diluted in 150 mM borate buffer, (boric acid), pH 7.0, with benzyl alcohol and trichlorobenzoic acid markers, separated into its constituents by CZE.
Figure 1C:
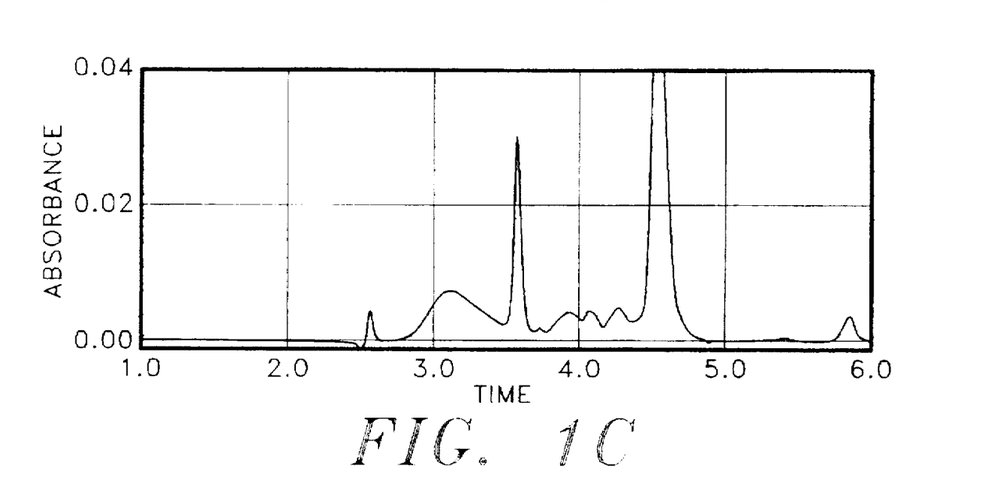
FIG. 1C is an electropherogram of a normal control serum sample diluted in 20 mM potassium phosphate, 75 mM sodium chloride buffer, pH 7.0, with benzyl alcohol and trichlorobenzoic acid markers, separated into its constituents by CZE.
Figure 1D:
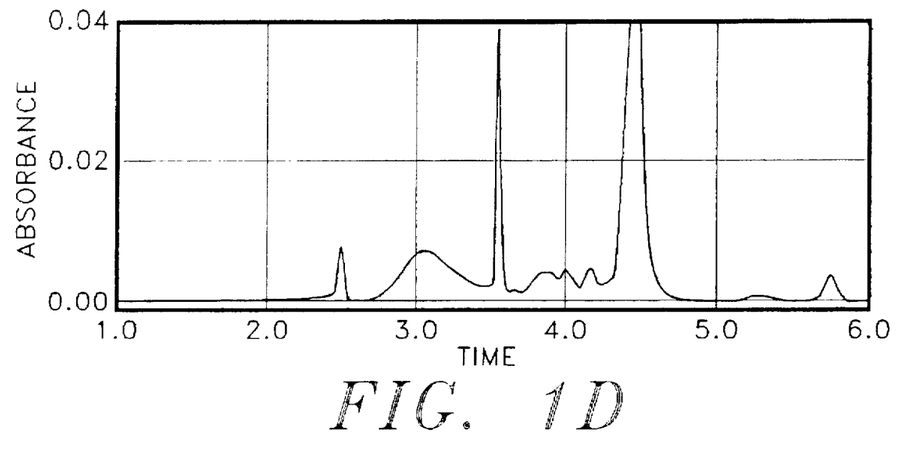
FIG. 1D is an electropherogram of a normal control serum sample diluted in 20 mM potassium phosphate, 75 mM sodium chloride buffer, pH 10.0, with benzyl alcohol and trichlorobenzoic acid markers, separated into its constituents by CZE.

When 150 mM borate was used in place of storage buffer, serum proteins in the beta region were resolved into a faster migrating smaller and a larger slower migrating peak (see FIGS. 1A and 1B). Moreover, when borate buffer, pH 7 replaced storage buffer, resolution of serum proteins in the beta region was unexpectedly improved (see FIG. 1B) over the original SPE diluent, 150 mM borate, pH 10 (FIG. 1A). The two peaks in the beta region, which presumably correspond to complement and transferrin, were much sharper and better separated in FIG. 1B. By comparison, phosphate buffer, at either pH 7 or 10, (FIGS. 1C and 1D) gave only a single sharp peak in the beta region that was not resolved into two peaks for complement and transferrin. This experiment suggested that the presence of borate in the sample enhances resolution of serum proteins, especially in the beta zone.

Example 2
Borate Dose Response

This study was conducted with TES buffer, to avoid any possible interaction between phosphate and borate, which might affect the results. Buffers were prepared with 10 mM TES plus the desired amount of sodium tetraborate, adjusted to pH 7.0 with 6N HCl, then NaCl was added to reach a final conductivity equivalent to that of running buffer. Thus, as the concentration of borate increases, the concentration of sodium chloride decreases. For the highest borate concentration (40 mM tetraborate) the conductivity was slightly higher than running buffer without the addition of NaCl. ID Zone was run under SPE conditions.

Figure 2A:
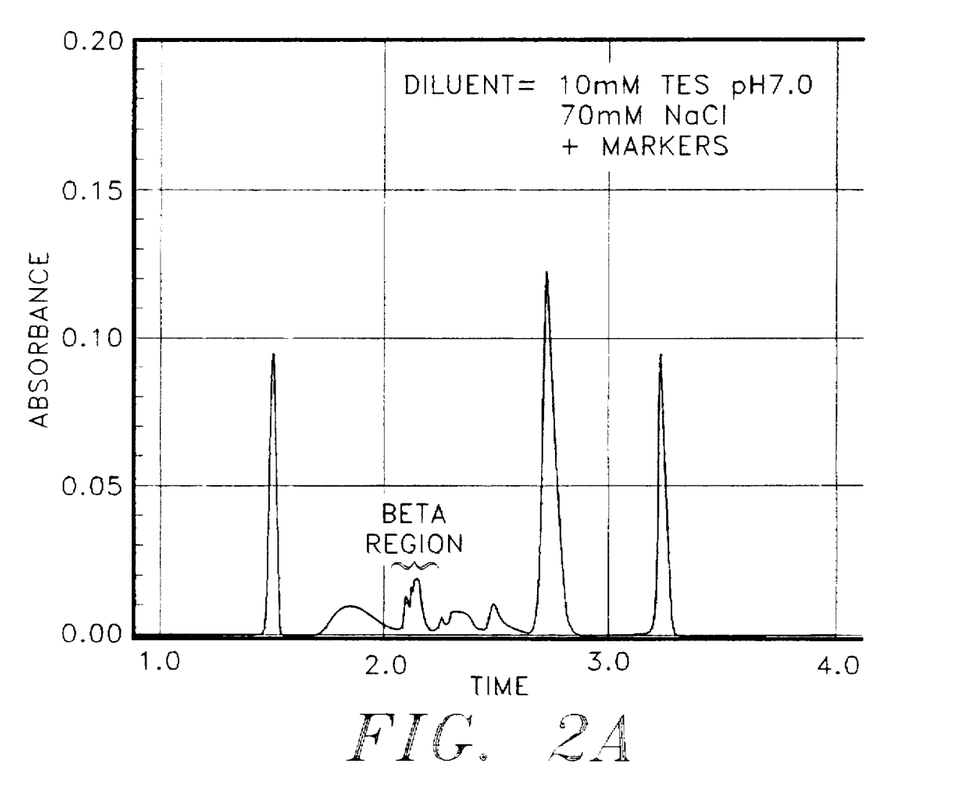
FIG. 2A is a first electropherogram of a normal control serum sample, diluted in 10 mM TES, 70 mM NaCl, pH 7.0, with benzyl alcohol and trichlorobenzoic acid markers, separated into its constituents by CZE.
Figure 2B:
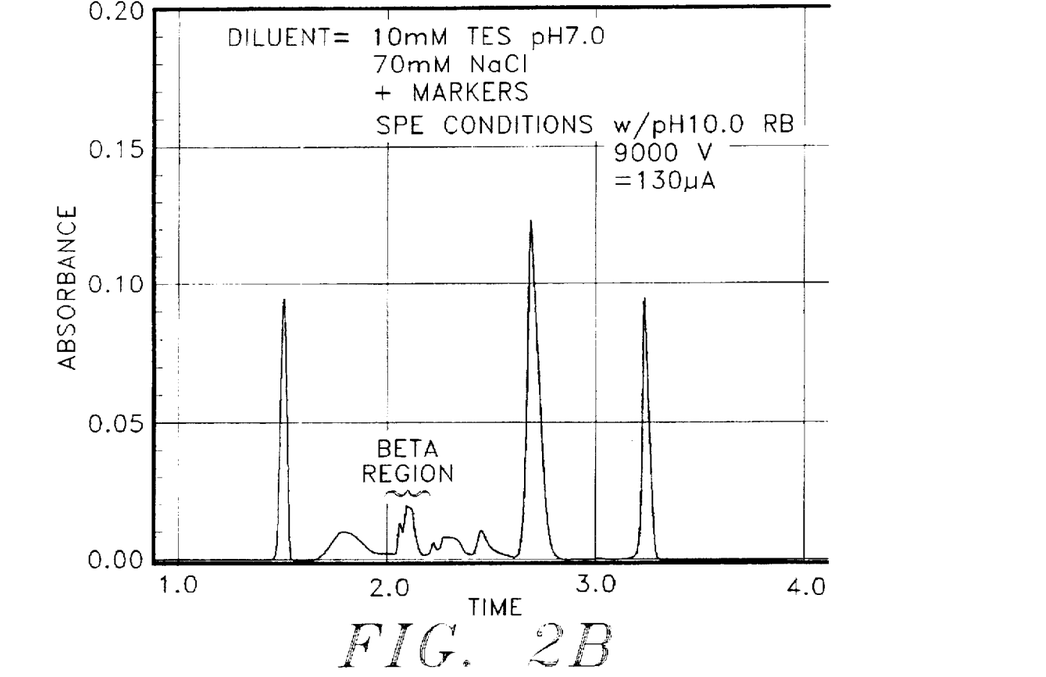
FIG. 2B is a second electropherogram of the same normal serum control sample as FIG. 2A separated into its constituents by CZE under identical conditions.
Figure 3:
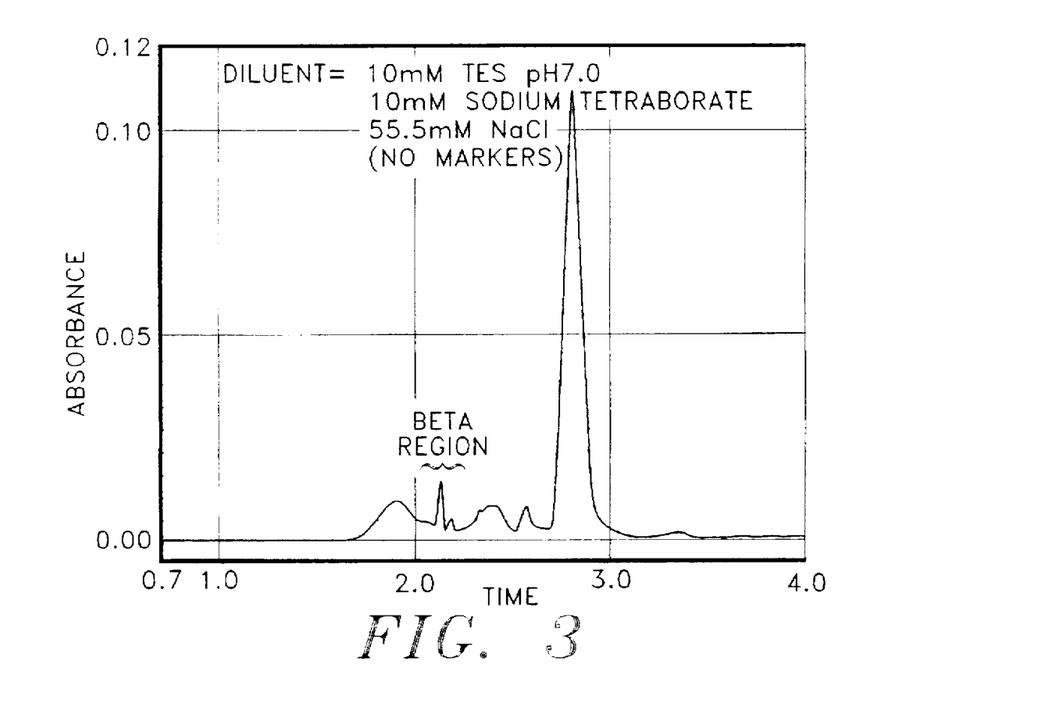
FIG. 3 is an electropherogram of the same normal serum control sample as FIGS. 2A and 2B, diluted in 10 mM TES, 10 mM sodium tetraborate, and 55.5 mM NaCl, pH 7.0 separated into its constituents by CZE.

FIGS. 2A and 2B are representative electropherograms showing the split and variable beta regions that are produced when TES buffers without borate are used. When the buffer includes around 5 to 20 mM tetraborate, e.g. see FIG. 3, two well defined peaks appear within the beta region. Moreover the morphology of the peaks remained essentially the same when the experimental conditions were replicated. Above 20 mM tetraborate the morphology of the scan does not change greatly but appears to become less reproducible with repetitive samples (not shown). Consequently, the most reproducible electropherograms of the serum proteins in the beta region occurred within a tetraborate concentration range of about 5 to about 20 mM.

Example 3
5 mM vs 10 mM Tetraborate

Sample diluents with 10 mM TES as the buffer salt plus 5 or 10 mM borate, pH 7.0 were used to dilute ID Zone samples. Thirty replicates of each test diluent were run under SPE conditions. Use of 5 mM tetraborate in the diluent still allowed significant variability in the beta region (not shown here), mostly in the form and number of shoulders to the main peak. However, the use of 10 mM tetraborate in the diluent yielded a very reproducible scan, as in FIG. 3, with two peaks in the beta region.

Example 4
Replace TES with Phosphate

Figure 4A:
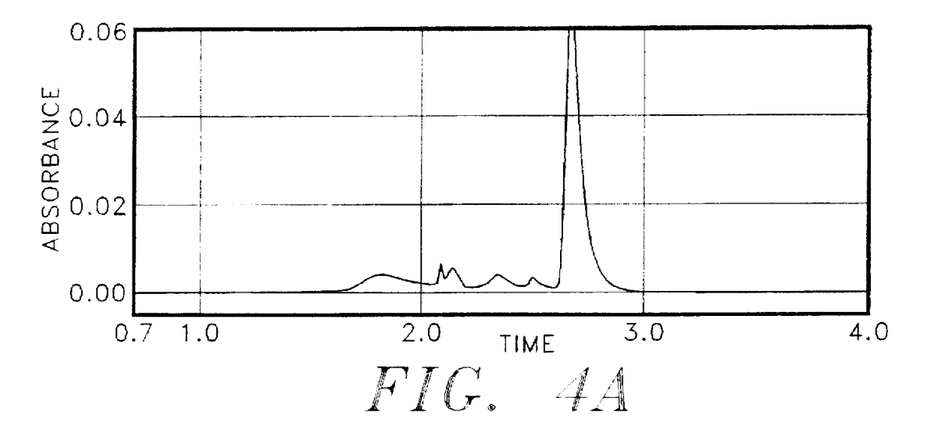
FIG. 4A is an electropherogram of a normal control serum sample diluted in 20 mM sodium phosphate, 10 mM sodium tetraborate, 0.1% sodium azide, and 29.6 mM NaCl, pH 7.0, separated into its constituents by CZE.
Figure 4B:
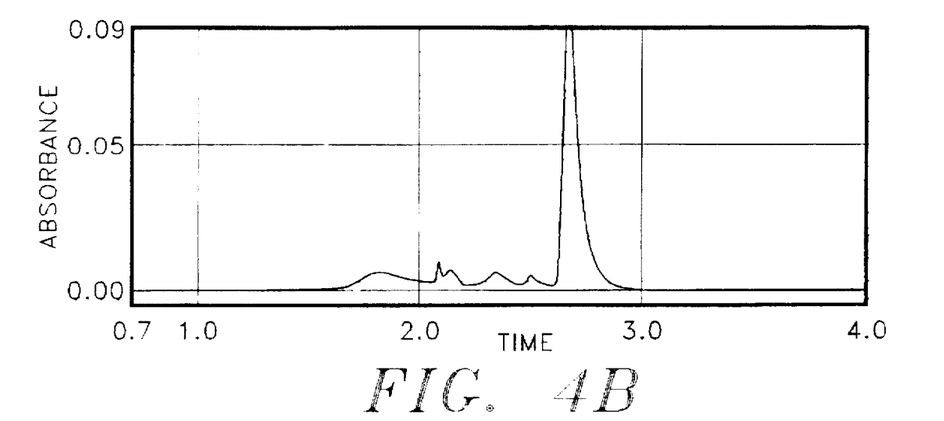
FIG. 4B is a second electropherogram of the same normal control serum sample as in FIG. 4A separated into its constituents by CZE under identical conditions.

Sample diluent was prepared with 20 mM monobasic sodium phosphate, 10 mM sodium tetraborate, 0.1% sodium azide and 29.6 mM NaCl, pH 7.0. The conductivity of the diluent was equivalent to running buffer, i.e. about 7.0 mMho. This diluent yielded an electropherogram very similar to that in FIG. 3, with two well resolved peaks in the beta region. When the electrophoretic separation was repeated under identical conditions, essentially the same profile was produced (see FIGS. 4A and 4B). Therefore, a phosphate buffered saline, pH 7.0, with 10 mM tetraborate added provides an acceptable and reproducible electropherogram.

Example 5
Boric Acid and Phosphate Buffers

The use of boric acid in the sample diluent/storage buffer was also tested. Moreover, increasing concentrations of potassium phosphate monobasic and/or dibasic were included to adjust the pH to 7.0 and to improve the buffering capacity. Maintaining a neutral pH may be necessary when storing a reagent, such as an antibody attached to a solid support.

The following buffers were prepared:

1) 143.4 mM borate (boric acid) 4.4 mM potassium dibasic
2) 150 mM borate (boric acid) 7.5 mM potassium phosphate dibasic 2 mM potassium phosphate monobasic
3) 150 mM borate (boric acid) 10 mM potassium phosphate dibasic 2 mM potassium phosphate monobasic
4) 150 mM borate (boric acid) 12.5 mM potassium phosphate dibasic 3 mM potassium phosphate monobasic
5) 150 mM borate (boric acid) 15 mM potassium phosphate dibasic 5 mM potassium phosphate monobasic When any or these boric acid/phosphate buffers were used as sample diluent/storage buffer as in Example 1, the resulting electropherograms displayed two well resolved peaks in the beta zone (not shown). Thus, boric acid was a suitable source of borate for the storage buffer/sample diluent. Moreover, the increased phosphate concentrations did not cause significant changes in the improved peak morphology obtained in the presence of borate.

The buffering capacity was compared to that of ICS Buffer by observing pH changes while adding small amount (20 μL each time) of 5N NaOH (Table 1) and 6N HCl (Table 2). As a general rule, the buffering capacity at about pH 7 was improved by increasing phosphate concentrations.

TABLE 1

| | | | | | | |
|---|---|---|---|---|---|---|
| pH of Test Buffers after addition of 5N NaOH | | | | | | |
| 5N NaOH added (μl) | ICS Buffer | 143 mM $H_3BO_3$ 4 mM $K_2PO_4$ | 150 mM $H_3BO_3$ 7.5 mM $K_2PO_4$ 2 mM $KH_2PO_4$ | 150 mM $H_3BO_3$ 10 mM $K_2PO_4$ 2 mM $KH_2PO_4$ | 150 mM $H_3BO_3$ 12.5 mM $K_2PO_4$ 3 mM $KH_2PO_4$ | 150 mM $H_3BO_3$ 15 mM $K_2PO_4$ 5 mM $KH_2PO_4$ |
| 0 | 7.00 | 6.98 | 6.99 | 7.00 | 7.02 | 6.99 |
| 20 | 7.22 | 7.25 | 7.20 | 7.18 | 7.17 | not tested |
| 40 | 7.50 | 7.46 | 7.40 | 7.34 | 7.32 | 7.26 |
| 60 | 7.98 | 7.63 | 7.56 | 7.49 | not tested | not tested |
| 80 | 10.28 | 7.76 | 7.70 | 7.61 | 7.57 | 7.5 |
| 100 | 10.92 | 7.88 | 7.81 | 7.72 | not tested | not tested |
| 120 | not tested | 7.98 | 7.91 | 7.83 | 7.78 | 7.71 |
| 140 | not tested | 8.07 | 8.00 | 7.91 | not tested | not tested |
| 160 | not tested | not tested | 8.07 | 8.00 | 7.95 | 7.89 |
| 180 | not tested | not tested | 8.15 | 8.08 | not tested | not tested |
| 200 | not tested | not tested | 8.21 | 8.14 | 8.10 | 8.04 |

TABLE 2 pH of Test Buffers after addition of 6N HCl

| 6N HCL added (µl) | ICS Buffer | 143 mM $H_3BO_3$ 4 mM $K_2PO_4$ | 150 mM $H_3BO_3$ 7.5 mM $K_2PO_4$ 2 mM $KH_2PO_4$ | 150 mM $H_3BO_3$ 10 mM $K_2PO_4$ 2 mM $KH_2PO_4$ | 150 mM $H_3BO_3$ 12.5 mM $K_2PO_4$ 3 mM $KH_2PO_4$ | 150 mM $H_3BO_3$ 15 mM $K_2PO_4$ 5 mM $KH_2PO_4$ |
|---|---|---|---|---|---|---|
| 0 | 6.96 | 7.00 | 7.00 | 6.99 | 7.01 | 6.98 |
| 20 | 6.74 | 6.45 | 6.68 | 6.74 | 6.80 | not tested |
| 40 | 6.52 | 3.14 | 6.22 | 6.43 | 6.56 | 6.62 |
| 60 | 6.25 | not tested | 3.55 | 5.91 | 6.27 | not tested |
| 80 | 5.92 | not tested | not tested | 3.12 | 5.74 | 6.12 |
| 100 | 5.45 | not tested | not tested | not tested | not tested | 5.62 |
| 120 | not tested | not tested | not tested | not tested | not tested | 3.29 |

Example 6
Buffer Additives

The effects of additional components in the 150 mM borate (boric acid), 15 mM potassium phosphate dibasic, 5 mM potassium phosphate monobasic, pH 7.0 buffer were studied. The tested components and their concentrations are listed below:

1) 0, 40 mM, and 75 mM sodium chloride;
2) 0.1% w/v sodium azide; and
3) 4% polyethylene glycol. The electrophoretic profile obtained after using buffers with the above listed components as sample diluent showed no significant differences in peak morphology from electropherograms obtained using borate buffers lacking the additional components.

Although the present invention has been described in considerable detail with reference to certain preferred versions, other versions are possible. For example, other buffer compounds having an effective buffering capacity within the range of about pH 6 to 8 may be used in the sample diluent/storage buffer. Therefore, the spirit and scope of the appended claims should not be limited to the description of the preferred versions contained herein.

What is claimed is:

1. A composition useful as a storage buffer or sample diluent prior to capillary electrophoresis, comprising:
   a) water;
   b) a borate compound present in an amount of about 5 to about 150 mM;
   c) a buffer compound and a pH modifier present in an amount sufficient to adjust the pH to between about 6 to 8; and
   d) a conductivity adjusting compound present in an amount sufficient to adjust the conductivity of the composition to between about 5 to about 8 mMho, wherein the conductivity adjusting compound is selected from the group consisting of sodium chloride, potassium chloride, and a mixture of sodium chloride and potassium chloride.

2. The composition of claim 1, wherein the borate compound is sodium tetraborate present in an amount of about 5 to about 40 mM.

3. The composition of claim 2, wherein the sodium tetraborate is present in an amount of about 10 mM.

4. The composition of claim 1, wherein the borate compound is boric acid present in an amount of about 20 to about 150 mM.

5. The composition of claim 4, wherein boric acid is present in an amount of about 40 mM.

6. The composition of claim 1, wherein the buffer compound is present in an amount of about 5 to 25 mM.

7. The composition of claim 1 wherein the buffer compound is selected from the group consisting of sodium phosphate, potassium phosphate, and 2-[tris (hydroxymethyl)methyl]amino-ethanesulfonic acid (TES).

8. The composition of claim 7, wherein the buffer compound is sodium phosphate.

9. The composition of claim 7, wherein the buffer compound is TES.

10. The composition of claim 8, wherein the sodium phosphate is present in an amount of about 20 mM.

11. The composition of claim 9, wherein the TES is present in an amount of about 10 mM.

12. The composition of claim 1 wherein the conductivity adjusting compound is present in an amount of about 1 to about 150 mM.

13. The composition of claim 12 wherein the conductivity adjusting compound is present in an amount of about 30 to about 120 mM.

14. The composition of claim 13 wherein the conductivity adjusting compound is present in an amount of about 75 mM.

15. The composition of claim 1 wherein the pH modifier is selected from the group consisting of sodium hydroxide, hydrochloric acid, and potassium phosphate.

16. A composition useful as a storage buffer or sample diluent prior to capillary electrophoresis, comprising:
   a) water;
   b) a borate compound present in an amount of about 5 to about 150 mM;
   c) a buffer compound and a pH modifier present in an amount sufficient to adjust the pH to between about 6 to 8;
   d) a conductivity adjusting compound present in an amount sufficient to adjust the conductivity of the composition to between about 5 to about 8 mMho; and
   e) a sample selected from the group consisting of whole blood, plasma, serum, urine, and cerebrospinal fluid.

17. A composition useful as a storage buffer or sample diluent prior to capillary electrophoresis, comprising:
   a) water;
   b) a borate compound present in an amount of about 5 to about 150 mM;
   c) a buffer compound and a pH modifier present in an amount sufficient to adjust the pH to between about 6 to 8;
   d) a conductivity adjusting compound present in an amount sufficient to adjust the conductivity of the composition to between about 5 to about 8 mMho; and e) at least one external marker selected from the group consisting of an ionic species and a neutral charge species.

18. The composition of claim 17 wherein the external marker ionic species is selected from the group consisting of formic acid, acetic acid, benzo-phosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chloro-benzo naphthalinic acid, chloro-naphthyl sulfonic acid, tetra-iodo benzo naphthyl sulfonic acid, and di-iodo anthracenyl sulfonic acid.

19. The composition of claim 17 wherein the external marker neutral charge species is selected from the group consisting of mesityl oxide, isopropanol, methanol, ethanol, ethylene glycol, dimethylformamide (DMF), formamide, protected peptides and protected amino acids.

20. The composition of claim 17 wherein the at least one external marker comprises benzyl alcohol and 2,4,6 trichlorobenzoic acid.

21. A composition useful as a storage buffer or sample diluent prior to immunosubtraction analysis of a sample constituent by capillary electrophoresis, comprising:
    a) water;
    b) a borate compound present in an amount of about 5 to about 150 mM;
    c) a buffer compound and a pH modifier present in an amount sufficient to adjust the pH to between about 6 to 8;
    d) a conductivity adjusting compound present in an amount sufficient to adjust the conductivity of the composition to between about 5 to about 8 mMho;and
    e) at least one specific binding partner to the sample constituent.

22. The composition of claim 21, wherein the specific binding partner is capable of being substantially removed from the composition.

23. The composition of claim 22, wherein the specific binding partner comprises a substance capable of binding to an insolubilized material.

24. The composition of claim 23, wherein the specific binding partner comprises an anti-human antibody.

25. The composition of claim 24, wherein the specific binding partner comprises an anti-human immunoglobulin antibody.

26. A composition for use as a storage buffer or sample diluent prior to capillary electrophoresis, comprising:
    a) water;
    b) sodium tetraborate present in an amount of about 10 mM;
    c) sodium phosphate present in an amount of about 20 mM;
    d) sodium chloride present in an amount sufficient to adjust the conductivity of the composition to about 7 mMho; and
    e) a pH modifier present in an amount sufficient to adjust the pH to about 7.

27. A test kit for preparing samples for serum protein electrophoresis comprising:
    (a) a first container comprising a composition comprising:
        i) water;
        ii) a borate compound present in an amount of about 5 to about 150 mM;
        iii) a buffer compound and a pH modifier present in an amount sufficient to adjust the pH to between about 6 to 8; and
        iii) a conductivity adjusting compound present in an amount sufficient to adjust the conductivity of the composition to between about 5 to about 8 mMho; and
    (b) a second container for retaining at least one sample.

28. A test kit according to claim 27, further comprising:
    (c) a third container comprising a composition useful as a storage buffer or sample diluent prior to capillary electophoresis, the composition comprising:
        i) water;
        ii) a borate compound present in an amount of about 5 to about 150 mM;
        iii) a buffer compound and a pH modifier present in an amount sufficient to adjust the pH to between about 6 to 8;
        iv) a conductivity adjusting compound present in an amount sufficient to adjust the conductivity of the composition to between about 5 to about 8 mMho; and
        v) at least one external marker selected from the group consisting of an ionic species and a neutral charge species.

29. A test kit for preparing samples for capillary electrophoretic immunosubtraction, comprising:
    (a) a first container comprising at least one composition according to claim 17; and
    (b) a second container comprising a composition useful as a storage buffer or sample diluent prior to immunosubtraction analysis of a sample constituent, the composition comprising:
        i) water;
        ii) a borate compound present in an amount of about 5 to about 150 mM;
        iii) a buffer compound and a pH modifier present in an amount sufficient to adjust the pH to between about 6 to 8;
        iv) a conductivity adjusting compound present in an amount sufficient to adjust the conductivity of the composition to between about 5 to about 8 mMho- ;and
        v) at least one specific binding partner to the sample constituent.

30. A test kit according to claim 29 wherein the second container comprises a multiplicity of chambers, wherein each chamber further comprises a different specific binding partner.

31. A method of preparing a sample for capillary electrophoresis comprising the steps of:
    a) measuring an aliquot of a clinical sample, the sample selected from the group consisting of whole blood, plasma, serum, urine, and cerebrospinal fluid; and
    b) diluting the sample with 1 to 300 parts of a composition comprising:
        i) water,
        ii) a borate compound present in an amount of about 5 to about 150 mm;
        iii) a buffer compound and a pH modifier present in an amount sufficient to adjust the pH to between about 6 to 8; and
        iii) a conductivity adjusting compound present in an amount sufficient to adjust the conductivity of the composition to between about 5 to about 8 mMho.

32. A method of preparing a sample for capillary electrophoresis immunosubtraction comprising the steps of:
    a) measuring an aliquot of a clinical sample, the sample selected from the group consisting of whole blood, plasma, serum, urine, and cerebrospinal fluid; and b) diluting the sample with 1 to 300 parts of the composition of claim 22.

33. A composition useful as a storage buffer or sample diluent prior to capillary electrophoresis, comprising:
   a) water;
   b) a borate compound present in an amount of about 5 to about 150 mM;
   c) a buffer compound and a pH modifier present in an amount sufficient to adjust the pH to between about 6 to 8, wherein the pH modifier is selected from the group consisting of sodium hydroxide, hydrochloric acid, and potassium phosphate; and
   d) a conductivity adjusting compound present in an amount sufficient to adjust the conductivity of the composition to between about 5 to about 8 mMho.

34. The composition of claim 33, wherein the borate compound is selected from the group consisting of sodium tetraborate and boric acid.

35. The composition of claim 33, wherein the borate compound is sodium tetraborate present in an amount of about 5 to about 40 mM.

36. The composition of claim 35, wherein the sodium tetraborate is present in an amount of about 10 mM.

37. The composition of claim 33, wherein the borate compound is boric acid present in an amount of about 20 to about 150 mM.

38. The composition of claim 37, wherein the boric acid is present in an amount of about 40 mM.

39. The composition of claim 33, wherein the buffer compound is present in an amount of about 5 to 25 mM.

40. The composition of claim 33, wherein the buffer compound is selected from the group consisting of sodium phosphate, potassium phosphate, and 2-[tris(hydroxymethyl)methyl]amino-ethanesulfonic acid (TES).

41. The composition of claim 40, wherein the buffer compound is sodium phosphate.

42. The composition of claim 41, wherein the sodium phosphate is present in an amount of about 20 mM.

43. The composition of claim 40, wherein the buffer compound is TES.

44. The composition of claim 43, wherein the TES is present in an amount of about 10 mM.

45. The composition of claim 33, wherein the conductivity adjusting compound is present in an amount of about 1 to about 150 mM.

46. The composition of claim 45, wherein the conductivity adjusting compound is present in an amount of about 30 to about 120 mM.

47. The composition of claim 46, wherein the conductivity adjusting compound is present in an amount of about 75 mM.

* * * * *